US012011282B2

(12) United States Patent
Najafi et al.

(10) Patent No.: US 12,011,282 B2
(45) Date of Patent: Jun. 18, 2024

(54) INSTRUMENTED TRAIL MAKING TASK (iTMT)

(71) Applicants: Baylor College of Medicine, Houston, TX (US); The United States of America as represented by the Department of Veterans Affairs, Washington, DC (US); Arizona Broad of Regents on behalf of Arizona State University, Tucson, AZ (US)

(72) Inventors: Bijan Najafi, Houston, TX (US); Javad Razjouyan, Houston, TX (US); He Zhou, Houston, TX (US); Mark Kunik, Bellaire, TX (US)

(73) Assignees: Baylor College of Medicine, Houston, TX (US); Arizona Board of Regents on behalf of Arizona State University, Tuscon, AZ (US); The United States of America as represented by the Department of Veterans Affairs, Washington, DC (US)

( * ) Notice: Subject to any disclaimer, the term of this patent is extended or adjusted under 35 U.S.C. 154(b) by 999 days.

(21) Appl. No.: 16/334,571

(22) PCT Filed: Sep. 18, 2017

(86) PCT No.: PCT/US2017/052102
§ 371 (c)(1),
(2) Date: Mar. 19, 2019

(87) PCT Pub. No.: WO2018/053445
PCT Pub. Date: Mar. 22, 2018

(65) Prior Publication Data
US 2021/0290148 A1    Sep. 23, 2021

Related U.S. Application Data

(60) Provisional application No. 62/396,671, filed on Sep. 19, 2016.

(51) Int. Cl.
G16H 50/30 (2018.01)
A61B 5/00 (2006.01)
A61B 5/11 (2006.01)

(52) U.S. Cl.
CPC .......... *A61B 5/4088* (2013.01); *A61B 5/1124* (2013.01); *A61B 5/6829* (2013.01); *G16H 50/30* (2018.01); *A61B 2562/0219* (2013.01)

(58) Field of Classification Search
CPC ... A61B 5/4088; A61B 5/1124; A61B 5/6829; A61B 2562/0219; A61B 5/1121; G16H 50/30; G16H 40/63; G16H 50/20
(Continued)

(56) References Cited

U.S. PATENT DOCUMENTS 6,067,986 A * 5/2000 Kluger ................ A61B 5/1124
600/595
8,690,325 B1 * 4/2014 Straus ................. A61B 5/0002
351/200
(Continued)

FOREIGN PATENT DOCUMENTS

WO    WO-2011063248 A1 *  5/2011  .......... A61B 5/1124

OTHER PUBLICATIONS

Turner, Hack: The Nintendo Wii, 2007 MIT Technology Review, Jul. 2007 Issue (Year: 2007).*
(Continued)

*Primary Examiner* — Joshua B Blanchette
*Assistant Examiner* — Tran N Nguyen
(74) *Attorney, Agent, or Firm* — Norton Rose Fulbright US LLP

(57) ABSTRACT

An instrumented trail-making task (iTMT) platform includes a wearable sensor and interactive interface technology configured to identify cognitive-cognitive impairment in individuals such as older adults. The iTMT platform (Continued)

may be programmed with neuropsychological tests for assessing individuals. The iTMT may provide information on visual search, scanning, speed of processing, mental flexibility, and/or executive functions as well as physical biomarkers of motor performance including slowness, weakness, exclusion, and/or motor planning error. Results of tests administered by the iTMT system may be reported to a patient or caregiver and used in identifying cogni-tive-motor impairment among individuals suffering from cognitive impairment, dementia, and/or those with frailty status, and/or cognitive frailty, and/or high risk of falling, and/or high likelihood of decline in cognitive-motor over time.

35 Claims, 8 Drawing Sheets

(58) Field of Classification Search
USPC .......................................................... 705/2–3
See application file for complete search history.

(56) References Cited

U.S. PATENT DOCUMENTS

| 2002/0143240 | A1  | 10/2002 | Teicher et al. |              |
|--------------|-----|---------|----------------|--------------|
| 2003/0077556 | A1  | 4/2003  | French et al.  |              |
| 2004/0015103 | A1  | 1/2004  | Aminian et al. |              |
| 2005/0187436 | A1* | 8/2005  | Doniger        | A61B 5/16    |
|              |     |         |                | 128/920      |
| 2009/0027337 | A1* | 1/2009  | Hildreth       | G06F 3/0482  |
|              |     |         |                | 345/158      |
| 2010/0152623 | A1* | 6/2010  | Williams       | A61B 5/4082  |
|              |     |         |                | 600/595      |
| 2011/0230792 | A1* | 9/2011  | Sarig-Bahat    | A61B 5/1124  |
|              |     |         |                | 600/595      |
| 2012/0130266 | A1* | 5/2012  | Mathan         | A61B 5/313   |
|              |     |         |                | 600/544      |
| 2014/0025361 | A1* | 1/2014  | Greene         | G16H 50/30   |
|              |     |         |                | 703/11       |
| 2016/0100788 | A1  | 4/2016  | Sano et al.    |              |
| 2016/0217325 | A1  | 7/2016  | Bose et al.    |              |

OTHER PUBLICATIONS

Zhou, Instrumented Trail-Making Task to Differentiate Persons with No Cognitive Impairment, 2017, Amnestic Mild Cognitive Impairment, and Alzheimer Disease: A Proof of Concept Study. Gerontology. 2017;63(2):189-200 (Year: 2017).*

Najafi, Laboratory in a box: wearable sensors and its advantages for gait analysis, 2011, Annu Int Conf IEEE Eng Med Biol Soc., 6507-10 (Year: 2011).*

Mirelman, Association Between Performance on Timed Up and Go Subtasks and Mild Cognitive Impairment: Further Insights into the Links Between Cognitive and Motor Function, 2014, J Am Geriatr Soc., April ; 62(4): 673-678 (Year: 2014).*

Grewal, Sensor-Based Interactive Balance Training with Visual Joint Movement Feedback for Improving Postural Stability in Diabetics with Peripheral Neuropathy: A Randomized Controlled Trial, 2015, Gerontology, 61(6):567-74 (Year: 2015).*

Synnott, WiiPD—Objective Home Assessment of Parkinson's Disease Using the Nintendo Wii Remote, 2012, in IEEE Transactions on Information Technology in Biomedicine, vol. 16, No. 6, pp. 1304-1312, Nov. 2012 (Year: 2012).*

Lindenberger, Memorizing while walking: Increase in dual-task costs from young adulthood to old age, 2000, Psychology and Aging, 15(3), 417-436 (Year: 2000).*

Weimer, "Motor" Impairment in Asperger Syndrome: Evidence for a Deficit in Proprioception, 2001, Journal of developmental and behavioral pediatrics : JDBP. 22. 92-101 (Year: 2001).*

Bowie, Administration and interpretation of the Trail Making Test, 2006, Nat Protoc 1, 2277-2281, https://doi.org/10.1038/nprot.2006.390 (Year: 2006).*

Synnott, WiiPD—Objective Home Assessment of Parkinson's Disease Using the Nintendo Wii Remote, 2012, in IEEE Transactions on Information Technology in Biomedicine, vol. 16, No. 6, pp. 1304-1312, Nov (Year: 2012).*

* cited by examiner iTMT FIXED iTMT RANDOM iTMT NUMBER-LETTER

INSTRUMENTED TRAIL MAKING TASK (iTMT)

CROSS-REFERENCE TO RELATED PATENT APPLICATIONS

This application is a national phase application under 35 U.S.C. § 371 that claims priority to International Application No. PCT/US2017/052102 filed Sep. 18, 2017, which claims the benefit of priority of U.S. Provisional Patent Application No. 62/396,671 to Bijan Najafi et al. filed Sep. 19, 2016 and entitled "Instrumented Trail-Making Task (iTMT)," all of which are incorporated by reference herein.

FIELD OF THE DISCLOSURE

The instant disclosure relates to medical diagnostics and intervention. More specifically, certain portions of this disclosure relate to a computerized platform for evaluating cognitive and motor functions and cognitive frailty and improving motor and cognitive performance.

BACKGROUND

Dementia, cognitive, and motor impairment impose serous challenges to the world's medical care system as the population grows older for which early detection may be beneficial. Researchers have estimated that the number of adults with dementia will increase 2.5-4-fold by 2050 because of population aging. Mild Cognitive Impairment (MCI), which does not reach the threshold for dementia diagnosis, has a high prevalence at ~22% among US older adults. Decline in cognitive functions leads to a loss of independent function that has a wide-ranging impact on individuals, families, and healthcare systems. Loss of cognitive performance is also known to be associated with increased risk of adverse events post-intervention, complications of coexisting medical conditions, increased risk of falling, overall degradation in quality and satisfaction of life, decreased mobility, increased healthcare utilization, and/or substantial caregiver burden. On the other hand, motor impairment could lead to prolonged immobility, which in turn may lead to motor memory loss and cognitive impairment.

Current diagnosis of dementia and cognitive-motor impairment are initiated mostly on a clinician's suspicion, based on patient symptoms or caregivers' concerns, usually in a primary care setting. This is mainly due to the impracticality of current modalities, which are often not suitable for routine usage in busy clinics and/or outside of clinic including nursing homes and long term settings. Thus, it is not surprising that a recent report suggests that 50% of persons with dementia are not diagnosed, and most persons are not diagnosed until the late stages of the illness. This is of increasing concern, given that most investigators believe disease-modifying therapies will be most effective in the preclinical and early stages. This has created an urgent need for a robust and rapidly-administered cognitive assessment tool capable of identifying individuals in the earliest stages of cognitive decline and measuring subtle changes in cognitive-motor performance over time.

SUMMARY

Precise and early diagnosis of cognitive-motor impairment and dementia in the older population is important for providing intelligent and personalized interventions in early stages, and thus delaying further deteriorative progression and/or limiting the consequences of cognitive decline, such as increasing risk of falling and decreasing mobility. Early diagnosis of cognitive-motor decline offers several direct benefits to persons at risk. For example, detection can prompt evaluation of the patient for reversible causes of cognitive-motor decline. When the course of the disease is expected to be chronic and progressive, pharmacologic intervention may slow cognitive-motor decline and/or limit the consequences, such as increasing risk of falling and decreasing mobility. Early identification could also help identify and understand remediable contributions to cognitive-motor decline, such as substance use, medications, and sleep disorders. Perhaps most importantly, early diagnosis provides time for patients and families to prepare for future care and maximizes patients' opportunities to contribute to the care planning process. Thus, a proactive approach to diagnosis and intervention may improve the well-being of both persons with risk of dementia and family members involved in their care.

A tool to identify and track subtle changes in cognitive-motor impairment irrespective of setting is beneficial for early stage diagnosis and implementing effective intervention. In this context, physical frailty together with cognitive impairment (known as "cognitive frailty") has been shown to be a strong and independent predictor of cognitive decline over time. One embodiment of such a tool, described herein, is a wearable sensor and other components of an instrumented trail-making task (iTMT) platform. The instrumented trail-making task (iTMT) platform may have a wearable sensor and interactive interface technology configured to identify cognitive-motor impairment in individuals, such as older adults. The iTMT platform allows simultaneous assessment of cognitive impairment and physical frailties. The iTMT platform may be programmed with neuropsychological tests for assessing individuals. The iTMT may provide information on visual search, scanning, speed of processing, mental flexibility, and/or executive functions as well as physical markers of motor impairment such as slowness, weakness, motor-planning error, and exhaustion. In some embodiments, the iTMT system may be used for identifying cognitive-motor impairment among individuals suffering from Mild Cognitive Impediment (MCI), Alzheimer's Disease (AD), and other neurological diseases. In some embodiments, the iTMT system may be used for identifying Chemotherapy-Related Cognitive Impairment (CRCI) or "Chemo-brain" in cancer population. In some embodiments, the iTMT system may be used to identify physical frailty. Physical frailty may be determined based on measuring angular velocity from ankle sensor during iTMT test and different metrics extracted from this sensor allows quantifying key physical frailty phenotypes. Frailty phenotypes may include slowness, weakness, and exhaustion, and can be determined by shin angular velocity measured using a gyroscope during the ankle reaching task. In some embodiments, the iTMT system may be used to identify cognitive frailty, which can be confirmed when a subject has simultaneous frailty and cognitive impairment with a severity that depends on severity of frailty and cognitive impairment. When the sensor is worn on an ankle-joint, data from the ankle-sensor can be used for quantifying ankle velocity as a surrogate for slowness, its decline during the test as a surrogate for exhaustion, and ankle jerkiness as a surrogate for activity inefficiency, and the time consumed to reach all circles in the correct sequence as a surrogate for poor cognitive function and/or weakness. In some embodiments, the iTMT system may be used to track subtle changes in cognitive performance over time. In some embodiments, the iTMT system may be used to determine the pathway toward dementia or Alzheimer disease. In some embodiments, the system may simultaneously measure physical frailty and cognitive impairment (e.g., cognitive frailty).

The iTMT platform may administer tests to individuals that ask the individual to perform tasks to which the individual's response may be used in identifying cognitive-motor impairment. The wearable sensor may attach to the individual, such as on an arm or leg or foot or head, and movement of the wearable sensor may be monitored by a mobile device, personal computer, or another computing device communicating with the wearable sensor. In particular, individuals may be asked to perform body movements that translate, for example, a motion of an ankle-joint into an interactive interface. In some embodiments, the speed of joint point-to-point reaching movement during the iTMT test may be used as a predictor of gait speed and may be used for assessing slowness, motor performance, risk of falling, and/or frailty. Furthermore, the change in speed of point-to-point reaching movement and/or increase in jerkiness of movement during an iTMT test may be used as an indicator of exhaustion, weakness and/or for assessing frailty. Additionally, the difference between peak velocity during point-to-point reaching task and middle pathway of reaching task may be used to assess motor planning error, motor memory, and/or motor performance. Furthermore, by assessing high frequency of point-to-point reaching movement kinematics such as velocity and acceleration, the jerkiness of movement may be estimated. In some embodiments, the combination of assessing slowness of motion, jerkiness of movement, change in velocity of reaching from one to another, motor planning error, and/or the time to complete the iTMT is used to separate cognitive performance from motor performance. In some embodiments, comparison of parameters extracted from iTMT while the individual is executing the test during two different posture such as sitting and standing or sitting and lying or lying and standing increases the accuracy of assessing motor-performance. In some embodiments, the wearable sensor is worn on an upper limb of a bedbound patient, such as on a wrist during iTMT as non-weight bearing test. In some embodiments, iTMT is combined with other measurements such as an eye-tracking system to increase the accuracy of assessment of each independent subcomponent of iTMT such as visual search, scanning, speed of processing, mental flexibility, and/or executive functions. In some embodiments, iTMT is used as an exercise program to enhance cognitive-motor performance.

One example test involves requesting an individual to navigate a cursor between circles on a computer screen in a correct sequence. iTMT tests may include one or more tasks involving indexed-circles appearing on a computer screen, in which the tasks may be completed by moving the individual's ankle-joint. One example iTMT test displays a sequence numbers (e.g., 1-to-5) positioned in a fixed (iTMT-fixed) order. Another example iTMT test displays a sequence of numbers in a random (iTMTrandom) order. Yet another example iTMT test displays a sequence or numbers (e.g., 1-to-3) and letters (e.g., A&B) positioned in random order (iTMTnumber-letter). Individuals may be presented with one randomly-selected test of the three tests or a particular one of the three tests. Individuals may be asked to repeat certain tests multiple times. For example, each test may be repeated twice to examine test-retest reliability. Furthermore, multiple tests or tests under different conditions may be used to provide more granularity of an individual's condition. For example, tests may be administered during sitting and standing, and/or at different level of difficulties, to provide grading in severity of motor and cognitive performance impairment. In some embodiments, iTMT may include playing a game (e.g. a ninja fruit slicing game) instead of numbers and letters. For example, the test may include cutting a sequence of fruits with different color and shape in a pre-defined orders by moving the individual's ankle-joint.

Embodiments of the instrumented trail-making task (iTMT) platform provide a simple, safe, and practical testing system with promising results to identify cognitive-motor ability impairment among individuals including those suffering from Mild Cognitive Impairment (MCI) and Alzheimer's Disease (AD). The iTMT system provides information regarding visual search, scanning, speed of processing, mental flexibility, and executive functions as indicators of cognitive performance as well as slowness, weakness, exhaustion, jerkiness of movement, and motor planning error as indicators of motor performance or physical frailty. The iTMT system also provides information about cognitive frailty by simultaneous assessment of cognitive and motor performance. iTMT is sensitive to a variety of neurological impairments and processes in both adults and children, and is not dependent on an examiner's training and experience. iTMT is sensitive to subtle changes in cognitive-motor performance over time. Thus, some embodiments of the iTMT system, may analyze data recorded for an individual over a period of time during which numerous tests were administered to determine these changes in cognitive-motor-performance over time. Embodiments of an iTMT platform improve the feasibility, reliability, and accuracy of trail-making task (TMT) testing in identifying cognitive-motor impairment among individuals, including those suffering from MCI and AD.

According to one embodiment, a method may include presenting a series of requested motions to be performed by an individual; receiving motion data from a sensor recording the individual performing the series of requested motions; analyzing the received motion data to determine a cognitive-motor impairment score for the individual; and/or reporting the cognitive-motor impairment score for the individual. The report may also include a score based on a detection of cognitive frailty by identifying simultaneous presence of frailty and cognitive impairment. The method may be programmed as a computer program product for execution by a computing device to carry out certain steps of the method. The method may be carried out by a system comprising a wearable sensor comprising at least one motion sensor, wherein the wearable sensor is configured to record motion data from the at least one motion sensor and to transmit the motion data, and a computing device configured to receive the motion data transmitted by the wearable sensor and configured to perform certain steps of the method.

The foregoing has outlined rather broadly certain features and technical advantages of embodiments of the present invention in order that the detailed description that follows may be better understood. Additional features and advantages will be described hereinafter that form the subject of the claims of the invention. It should be appreciated by those having ordinary skill in the art that the conception and specific embodiment disclosed may be readily utilized as a basis for modifying or designing other structures for carrying out the same or similar purposes. It should also be realized by those having ordinary skill in the art that such equivalent constructions do not depart from the spirit and scope of the invention as set forth in the appended claims.

Additional features will be better understood from the following description when considered in connection with the accompanying figures. It is to be expressly understood, however, that each of the figures is provided for the purpose of illustration and description only and is not intended to limit the present invention.

BRIEF DESCRIPTION OF THE DRAWINGS

For a more complete understanding of the disclosed system and methods, reference is now made to the following descriptions taken in conjunction with the accompanying drawings.

DETAILED DESCRIPTION

Figure 1:
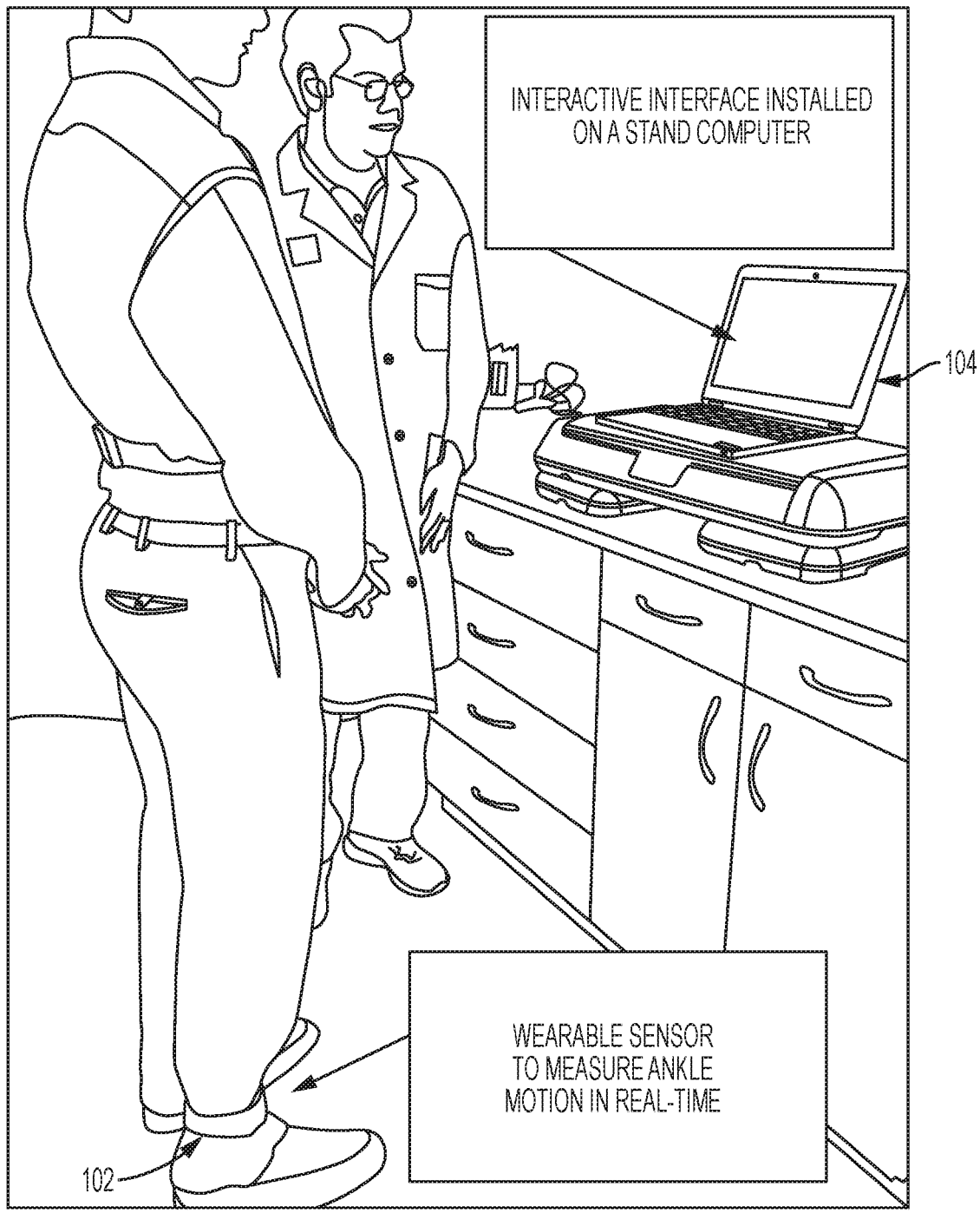
FIG. 1 is an illustration of an individual with a wearable sensor interacting with an interactive interface for administering an instrumented trail-making task (iTMT) neuropsychological test according to some embodiments of the disclosure.

FIG. 1 is an illustration of an individual with a wearable sensor interacting with an interactive interface for administering an instrumented trail-making task (iTMT) neuropsychological test according to one embodiment of the disclosure. The instrumented trail-making task (iTMT) platform 100 may include a wearable sensor 102, which may include one or more of an accelerometer, a gyroscope, and a magnetometer sensor. The wearable sensor 102 may include multiple sensors, such as up to five or more sensors. Some sensors may be configured for estimate spatio-temporal parameters of gait (e.g. gait speed and gait symmetry) without the need of performing gait test. Some sensors may be configured to measure inertial signals (e.g. acceleration, angular velocity, angle) perpendicular to a direction of a reaching task to improve the model for assessing balance, postural coordination, and motor performance. In some embodiments, the sensors are combined with other sensor units such as heart rate monitoring, respiration monitoring, and/or body temperature monitoring to assess changes in physiological parameters during iTMT test. This information can increase the accuracy of assessing frailty, risk of falling, physical fatigue, cognitive fatigue, and cognitive response to a physical stress. The sensing components of the wearable sensor 102 may be configured for estimation of angles and a position of the wearable sensor 102 during an iTMT test, such as to track an individual's movements. The wearable sensor 102 may also include a processor, memory, and communications circuitry (such as a wireless transceiver/receiver) for processing data from the sensing components and transmitting the sensor data to an interactive interface. In some embodiments, the data is transmitted to another device and processed in another location such as cloud, tablet, cell phone, or computer. In some embodiments, the transmitted sensor data may be processed data, such that the sensor data includes angles and positions or another representation of the data received from the sensing components. In some embodiments, the wearable sensor 102 wireless transceiver operates at 100 Hz frequency for real-time feedback in a virtual environment. Although only one wearable sensor 102 is shown in FIG. 1, sensor data may be collected from multiple locations on an individual or from multiple individuals simultaneously. For example, additional wearable sensors may be worn by an individual, such that coordination between motion of the ankle and hip during an iTMT reaching task can be assessed to provide further information about balance and motor performance. The sensor can also be attached to other body locations such as head, arm, lower back, or any other body segment while performing tasks.

The wearable sensor 102 may be configured in a housing having one or more attachment devices (such as string, hook-and-loop fasteners, straps, wraps, etc.) to attach to an individual. For example, during an iTMT test, the wearable sensor 102 may be attached to the individual's shin. In some embodiments, the wearable sensor 102 includes an elastic strap to allow tracking ankle motion in three dimensions. In some embodiments, the sensor is implemented inside of the individual's body, injected inside the body, or tattooed on the individual's skin. The movement of the wearable sensor 102 may be transmitted to an interactive interface installed on a personal computer 104 or other processing device. In some embodiments, portions of the interactive interface may be integrated with the wearable sensor 102. For example, the wearable sensor 102 may cast an iTMT test to a nearby display, collect sensor data during administration of the test, and analyze the sensor data to determine a cognitive-motor impairment score for the individual, and display a result of the iTMT test on the cast display or a display screen or other indicator integrated with the wearable sensor 102. In some embodiments the interactive interface could be computer laptop, desktop, tablet, cell phone, TV, eye-glasses, or any other means of visualization. In some embodiments, the feedback could be non-visual signals such as audio or vibratory feedbacks or combination of visual and non-visual feedbacks.

One advantage of the iTMT platform is the use of the low-cost, wearable sensor 102 to interact with the individual and estimate objective metrics free of bias from the examiner. Such a method is a better solution than conventional motion-tracking systems, such as video-based systems or game console controller-based systems. For example, when a camera is used to capture an individual's motion, a minimum distance of approximately two meters may be required between the camera and the individual. For older adults, this distance could be too far to see the computer screen and execute the tasks. Furthermore, camera-based systems require a continuous unobstructed sightline, which would be obstructed by, for example, a chair or other structure in front of the individual to be used as a mechanism to prevent falls during the test. Likewise, camera-based systems may be confused by a caretaker or administrator next to the subject during the test. Having a person nearby may be an important safety feature during the trail-making test in older adults, in particular, those with MCI and dementia, who have increased fall risk. The wearable sensor can be used during an iTMT test with a caretaker nearby. On the same note, force platforms, such as some game console controllers, restrict the base of support during testing, which may cause falls during dynamic tests. In addition, such controllers do not provide any information about joint angles, which may be useful inputs for the iTMT. Thus, using the wearable sensor 102 for the purpose of iTMT provides benefits with respect to conventional motion-tracking and virtual-reality alternatives, allowing easier and safer administration of the test in any preferred position with any auxiliary means (e.g., using a cane, walker, chair, etc. as support).

During an iTMT test, the interactive interface of the iTMT system may present a series of requested motions to be performed by an individual. The requested motions may be selected to examine cognitive (trail-making performance) as well as motor ability (ankle reaching task performance) of the individual. By moving the ankle with attached wearable sensor 102, the subject can navigate a cursor on the screen from a start circle to targets appearing on the same screen. The system may allow performing the same iTMT tests while sitting or standing. In some embodiments, the joint of interest for iTMT is the lower extremities (e.g., foot and ankle), however the wearable sensor 102 may also be located in different positions to monitor other joint segments.

In one embodiment of the interactive interface, the individual may be instructed to stand in front of a computer screen wearing the wearable sensor 102. For safety purposes, a study administrator may be present in the room for supervising the iTMT. After starting the iTMT test, the administrator may provide no further guidance and only the interactive interface provides the necessary guidance and instructions. The interactive interface may administer one or more tests. The tests may be selected in advance for the patient or randomly selection. Some examples of iTMT tests that may be administered are fixed order trail-making (iTMTfixed), random order trail-making (iTMTrandom), number-letter order trail-making (iTMTnumber-letter), and trail making to different shapes, different type of fruits, colors, etc.

During the trail-making tests, the individual navigates the cursor to targets displayed on a screen in a certain order by moving their ankle joint with attached wearable sensor 102. The individual may generally be expected to navigate the cursor to the right target within 0.5 to 2 seconds. The interactive interface may evaluate the amount of time the individual takes to navigate the cursor to the target and make determinations regarding the individual based on the time for each target in the administered test.

The platform may evaluate the pattern of ankle velocity during a point-to-point reaching task, estimate the time of initiation of movement from start point in respect to the time the targets are visualized on interactive interface, estimate the time for completing a point-to-point reaching task, estimate the magnitude and location of maximum peak velocity, and/or estimate the difference between location of peak velocity and middle pathway (i.e. 50% of time duration to complete the point-to-point reaching task) as shown in FIG. 5. In some embodiments, a jerkiness of movement may be determined by determining a high and low frequency component of a velocity signal and the ratio of high frequency to low frequency is defined as jerkiness of movement.

Some intermediate results may be displayed during the administration of the test. If the individual uses more than 2 seconds (too slow), the target circle may turn green as a visual cue. If the individual uses between 0.5 to 2 seconds (perfect), the border of the target circle may turn red, and the target circle will explode with a rewarding sound. If an individual makes a mistake in navigating to the wrong target, the individual may receive a visual and audio error signal. If the individual makes multiple (e.g., three) consecutive mistakes, the correct target may be made blinking as a visual cue to guide the individual to continue trail-making in the correct sequence. Other graphical or audio effects may be minimized to prevent distraction of the individual. This simplistic design of the graphical user interface allows the subject to focus on cognitive tasks, better focus on the iTMT test, and perceive errors (e.g., differences between the actual motor output and the desired motor output) during trail-making tasks. Other indexed targets or shapes could also be used, such as color-coded targets or using animals or symbols as targets instead of circle targets. For example, the test subject could be instructed to complete iTMT in a particular order, such as to reach to a target which include a picture of a bird, then to a picture of a cat, then to a picture of a dog, etc. The test could also be complicated or simplified by adding or reducing the number of target patterns or increasing or reducing the distance between home target (i.e. the start point) and reaching targets.

Figure 2A:
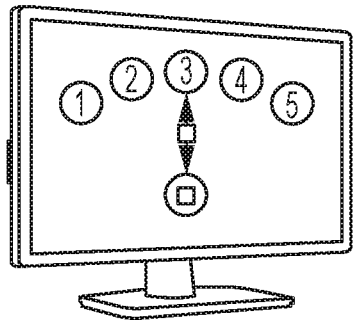
FIG. 2A is an illustration of a fixed order instrumented trail-masking task (iTMT) neuropsychological test according to some embodiments of the disclosure.

One example of an iTMT test that can be administered by the interactive interface is a fixed order trail-making task (iTMTfixed). FIG. 2A is an illustration of a fixed order instrumented trail-masking task (iTMT) neuropsychological test according to some embodiments of the disclosure. The iTMTfixed may have a low level of cognitive complexity. In this trail-making task, a plurality of circles (e.g., six circles) may be presented on the screen: one start circle in white and five target circles in yellow. The target circles may be located in a fanwise position in front of the start circle. Each target circle may have a number located in the center. From left to right, the five target circles may have fixed numbers 1, 2, 3, 4, and 5 in sequence. Although numbers are described, other types of labels may be used, such as letters, roman numerals, symbols, etc. At the beginning of the trail-making task, a position of the cursor may be automatically calibrated to the center of the white start circle. By rotating the ankle joint, an individual may navigate the cursor, using the wearable sensor 102, to the center of the first target circle (with number "1" inside). Then, the individual may navigate the cursor back to the center of the start circle, and then navigate the cursor to the second target circle (with number "2" inside), and then proceed similarly through the rest of the circles. Each time the interactive interface may monitor the amount of time consumed to navigate the cursor between circles and whether the cursor is being navigated to the correct circle. If the individual navigates the cursor to a wrong target circle, a visual and audio feedback indicating the mistake may be played. Then, the individual may navigate the cursor back to the start circle and continue the trail-making task from where the previous mistake was made. If the individual makes too many consecutive mistakes (e.g., three mistakes), a visual cue of a flashing of the correct target circle may appears to guide the individual to correct the sequence.

Figure 2B:
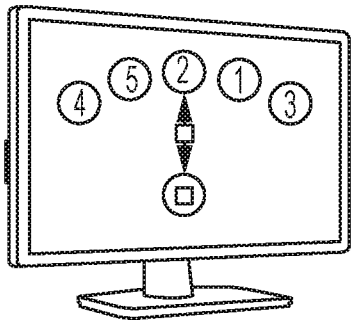
FIG. 2B is an illustration of a random order instrumented trail-masking task (iTMT) neuropsychological test according to some embodiments of the disclosure.

Another example of an iTMT test that can be administered by the interactive interface is a random order trail-making task (iTMTrandom). FIG. 2B is an illustration of a random order instrumented trail-masking task (iTMT) neuropsychological test according to some embodiments of the disclosure. The iTMTrandom test is similar to the fixed order, but the order of numbers located at the center of target circles is not fixed from left to right. At the beginning of each task measurement, numbers (e.g., 1, 2, 3, 4, and 5) are randomly placed in the target circles. Although numbers are described, other types of labels may be used, such as letters, roman numerals, symbols, etc. In this trail-making task, there may be no pattern to follow. The individual may need to observe and determine the correct target of the next move. The iTMTrandom test adds more cognitive challenges when compared with the fixed order.

Figure 2C:
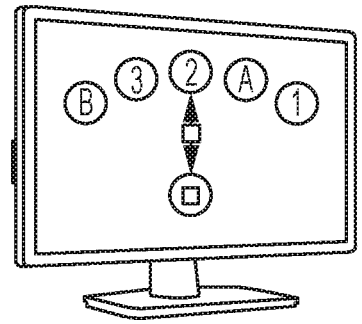
FIG. 2C is an illustration of a number-letter order instrumented trail-masking task (iTMT) neuropsychological test according to some embodiments of the disclosure.

A further example of an iTMT test that can be administered by the interactive interface is number-letter order trail-making task (iTMTnumber-letter). FIG. 2C is an illustration of a number-letter order instrumented trail-masking task (iTMT) neuropsychological test according to some embodiments of the disclosure. The iTMTnumber-letter has a higher level of cognitive complexity. In this task, not only the order of numbers in target circles is randomized, but also numbers are mixed with letters together. That is, instead of 1, 2, 3, 4, and 5, the target circles may be labeled 1, A, 2, B, and 3. Although numbers and letters are described, other mixed types of labels may be used, such as roman numerals, symbols, etc. The individual may be instructed to navigate the cursor to targets with numbers and letters alternately. For example, after navigating to target "1", instead of navigating to target "2", the individual should navigate the cursor to target "A". In this test, in addition to observing and finding the correct location of the next target, the individual also needs to remember switching between number and letter sequences. This makes the iTMTnumber-letter more cognitive-challenging than the fixed order and random order for subjects with cognitive impairment.

Figure 3:
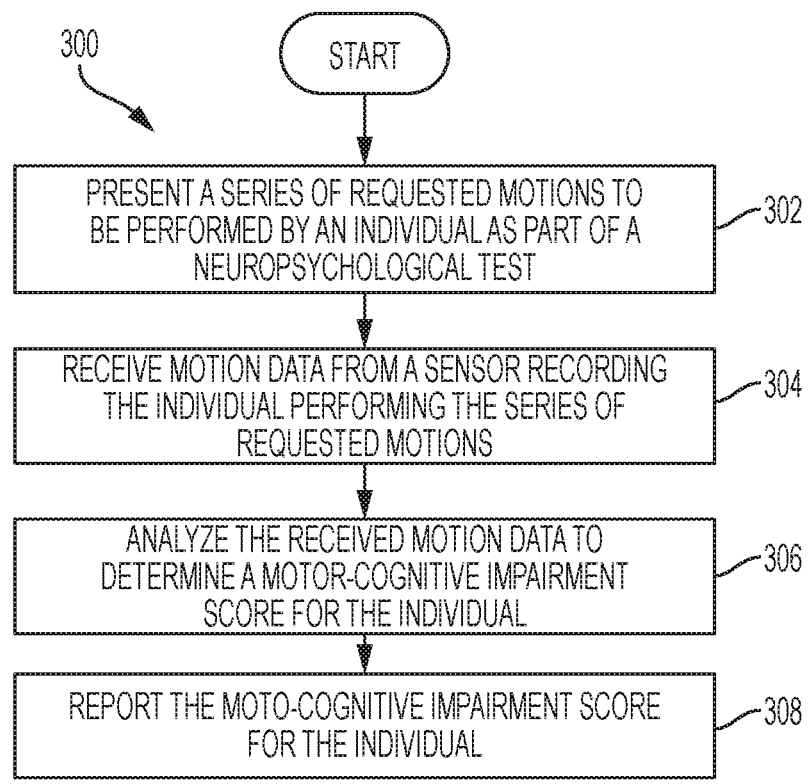
FIG. 3 is a flow chart illustrating an example method for an interactive interface to administer an instrumented trail-making task (iTMT) neuropsychological test according to some embodiments of the disclosure.

An example method is shown in FIG. 3 for administering a test, such as the tests described with reference to FIG. 2A, FIG. 2B, and FIG. 2C, on an iTMT platform, such as described with reference to FIG. 1. FIG. 3 is a flow chart illustrating an example method for an interactive interface to administer an instrumented trail-making task (iTMT) neuropsychological test according to one embodiment of the disclosure. A method 300 may begin with sensor calibration, establishing a communication link with the wearable sensor 102, or other initialization steps (not shown).

The method 300 may then proceed with administering one or more tests to the individual. At block 302, an interactive interface may present a series of requested motions to be performed by an individual as part of a neuropsychological test. For example, one of the patterns described with reference to FIG. 2A, FIG. 2B, or FIG. 2C may be presented to an individual wearing the wearable sensor 102. Next, at block 304, motion data may be received from the wearable sensor attached to the individual while the individual is performing the series of requested motions presented at block 302. The steps 302 and 304 may be repeated to test the individual multiple times using the same test or multiple times using different tests. Some intermediate results and/or further instruction may be presented to the individual during steps 302 and 304. For example, certain target circles may be highlighted or flashed to indicate to the individual that the individual navigated to the wrong target circle.

After the individual performs the tests administered during steps 302 and 304, the interactive interface may process the motion data to evaluate the individual for one or more metrics. At block 306, the motion data received during the course of the test may be analyzed to determine a cognitive-motor impairment score for the individual. Analysis at block 306 may include analyzing raw sensor data or analyzing summaries of the sensor data recorded during the test. For example, times to navigate to each target circle may be stored during the test. Analysis at block 306 may include averaging the time required for the individual to navigate to each target circle or calculating a total time required to complete the presented tasks. Other characteristics can be determined, such as counting a number of mistakes in performing the requested motions to determine a working memory performance and such as measuring a time elapsed between onset of movement and onset of display of virtual targets on the screen to estimate the ability of visual search, scanning, speed of processing, mental flexibility, and/or executive functions. Next, at block 308, the results of the test may be presented to the individual, such as by providing the results to the administrator who will then provide the results to the individual. The results may be, for example, a generic score ranging from 1 to 5 indicating cognitive health of the individual. The results may also be, for example, a more detailed report indicating likelihood or presence of certain conditions, such as Mild Cognitive Impairment (MCI) and Alzheimer's Disease (AD).

Figure 4:
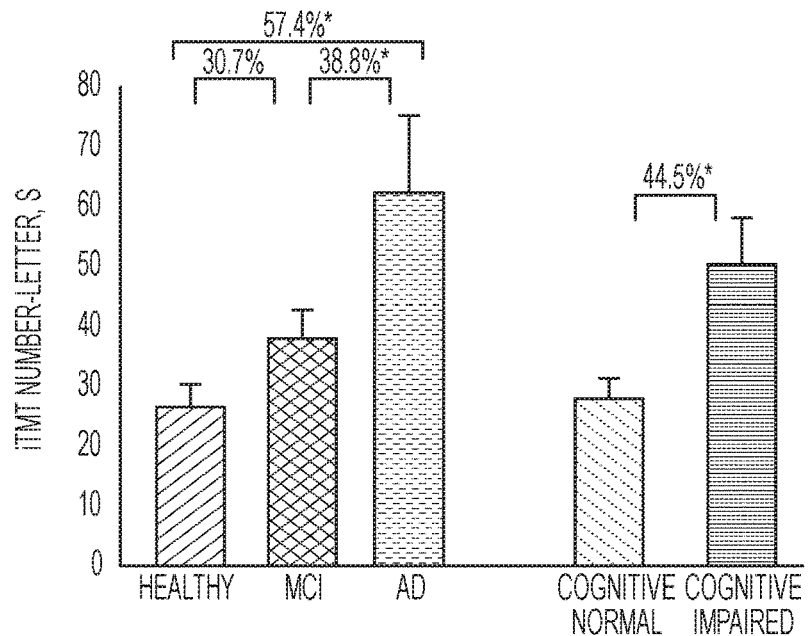
FIG. 4 is a graph illustrating the effectiveness of a number-letter order instrumented trail-masking task (iTMT) neuropsychological test according to some embodiments of the disclosure to identify individuals with healthy cognition, Mild Cognitive Impairment (MCI), and Alzheimer's Disease (AD), as well as differentiate cognitive normal and cognitive impaired individuals.

One embodiment of an iTMT platform was administered to test individuals with Mild Cognitive Impairment (MCI), Alzheimer's Disease (AD), or cognitive impairment. Some comparison data is shown in FIG. 4, which is a graph illustrating using a number-letter order instrumented trail-masking task (iTMT) neuropsychological test according to one embodiment of the disclosure to identify individuals with healthy cognition, Mild Cognitive Impairment (MCI), and Alzheimer's Disease (AD), as well as differentiate cognitive normal and cognitive impaired individuals. Significant differences between healthy and AD (mean difference=57.4%), MCI and AD (mean difference=38.8%), as well as cognitive normal and cognitive impaired (mean difference=44.5%) were observed.

Figure 5A:
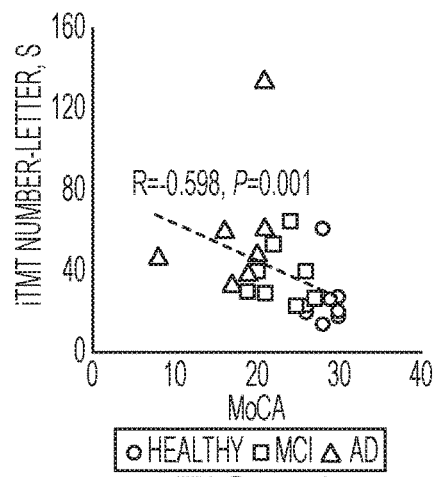
FIG. 5A is a graph illustrating a correlation between a number-letter order instrumented trail-masking task (iTMT) neuropsychological test according to some embodiments of the disclosure and conventional Montreal Cognitive Assessment (MoCA) test for identifying Mild Cognitive Impairment (MCI) and Alzheimer's Disease (AD).
Figure 5B:
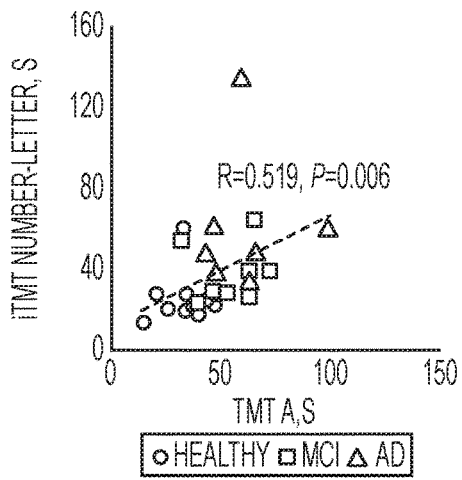
FIG. 5B is a graph illustrating a correlation between a number-letter order instrumented trail-masking task (iTMT) neuropsychological test according to some embodiments of the disclosure and conventional trail-making test (TMT-A) test for identifying Mild Cognitive Impairment (MCI) and Alzheimer's Disease (AD).
Figure 5C:
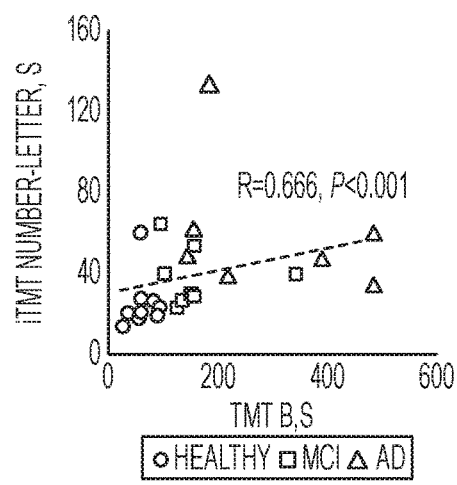
FIG. 5C is a graph illustrating a correlation between a number-letter order instrumented trail-masking task (iTMT) neuropsychological test according to some embodiments of the disclosure and conventional trail-making test (TMT-B) test for identifying Mild Cognitive Impairment (MCI) and Alzheimer's Disease (AD).

One embodiment of an iTMT platform was administered to test subjects and the test was confirmed to produce similar or better results regarding the test subjects as conventional testing regarding cognitive impairment. Some comparison data is shown in FIG. 5A, FIG. 5B, and FIG. 5C. FIG. 5A is a graph illustrating a correlation between a number-letter order instrumented trail-masking task (iTMT) neuropsychological test according to one embodiment of the disclosure and conventional Montreal Cognitive Assessment (MoCA) test for identifying Mild Cognitive Impairment (MCI) and Alzheimer's Disease (AD). FIG. 5B is a graph illustrating a correlation between a number-letter order instrumented trail-masking task (iTMT) neuropsychological test according to one embodiment of the disclosure and conventional trail-making test (TMT-A) for identifying Mild Cognitive Impairment (MCI) and Alzheimer's Disease (AD). FIG. 5C is a graph illustrating a correlation between a number-letter order instrumented trail-masking task (iTMT) neuropsychological test according to one embodiment of the disclosure and conventional trail-making test (TMT-B) for identifying Mild Cognitive Impairment (MCI) and Alzheimer's Disease (AD). A relatively good agreement was observed between the iTMTnumber-letter and MoCA ($r=-0.598$, $p=0.001$, as shown in FIG. 5A), as well as between iTMTnumber-letter and both TMT-A ($r=0.519$, $p=0.006$, as shown in FIG. 5B) and TMT-B ($r=0.666$, $p<0.001$, as shown in FIG. 5C).

An instrumented trail-making test (iTMT), such as in the embodiments described herein, may be used to identify cognitive impairment among older adults including those suffering from MCI and AD. This platform has a low cost of the wearable sensor 102 combined with an interactive interface installable on many computing devices, such as the personal computer 104 or a mobile device. The test is simple and can be administered in as little as one minute, making the test suitable for busy clinics. Administering the iTMT to patients with MCI and AD can be achieved without support or with minimum support from an administrator, while such individuals performing traditional tests often require significant involvement of an administrator. While the iTMT test is simple, short, safe, and easy to administer, the iTMT test has large to very large effect size to separate between groups with and without cognitive impairment as well as between healthy, MCI, and AD groups. In addition, good agreements with traditional cognitive assessment, such as MoCA and TMT-A and B, were observed. Furthermore, the iTMT test allows assessing simultaneously motor and cognitive performance unlike conventional cognitive assessment instruments. In some embodiments, conventional tests may also be performed on the individuals and the results combined to improve the ability of separation between motor and cognitive performance. While cognitive impairment can be identified with pencil- and paper-based screening tools, paper-based assessments are semi-subjective, time consuming, insensitive to subtle changes in cognitive frailty, and their accuracy is highly dependent on the examiner's experience and the patient's education level. Computerized versions of conventional cognitive screening tools have improved the utility of such measurements. However, they are not capable of monitoring motor performance (an essential component of physical frailty), and thus are not able to detect cognitive frailty, which is known to be a predictor of speed of cognitive decline over time.

Figure 6:
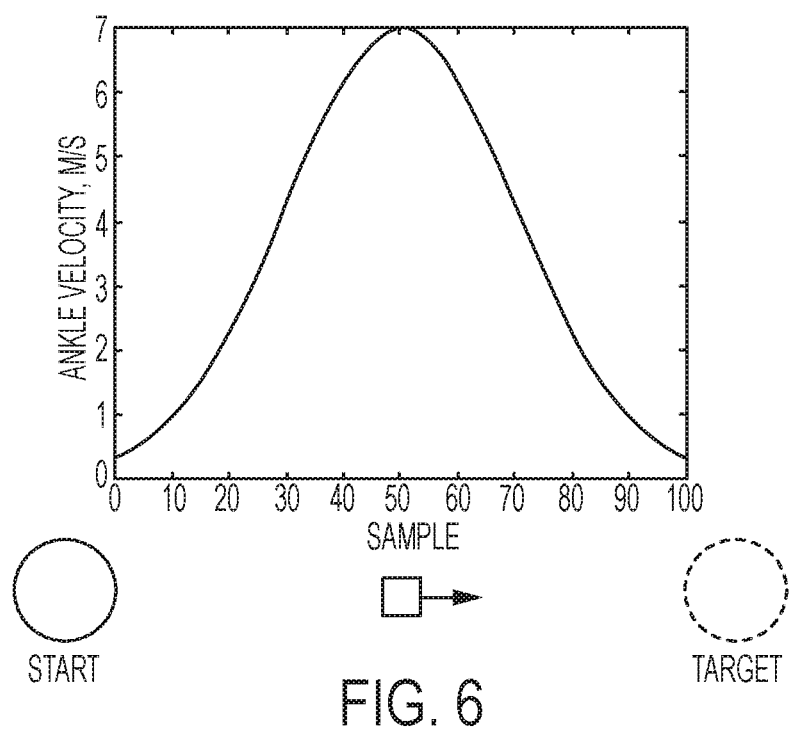
FIG. 6 is a graph illustrating the velocity pattern during a typical point-to-point reaching task according to some embodiments of the disclosure, in which a good cognitive-motor performance may be quantified by peak speed of reaching task, jerkiness of movement pattern, and/or dislocation of maximum peak respect to middle pathway.
Figure 7A:
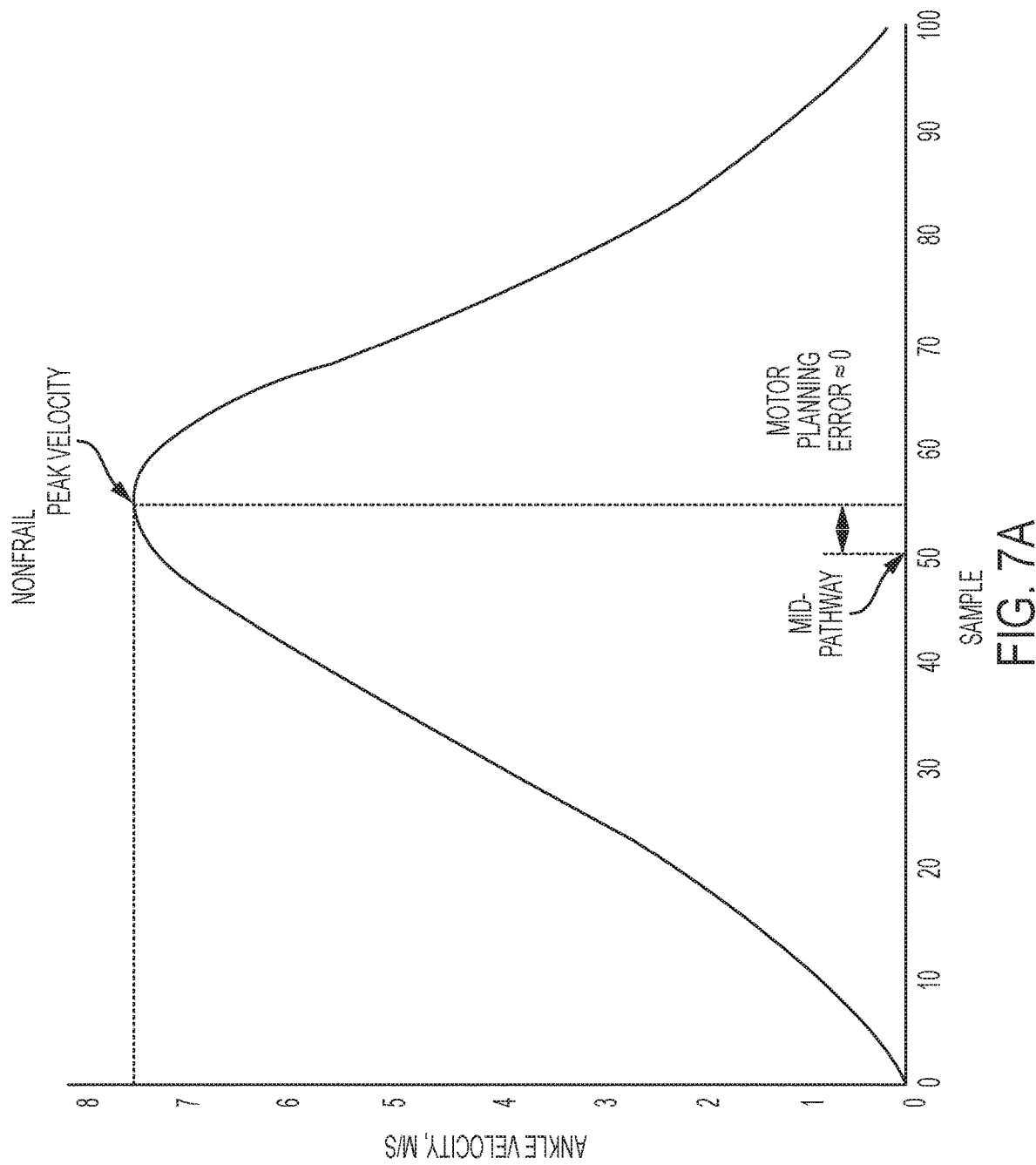
FIG. 7A is an illustration of a velocity pattern during point-to-point reaching task in a typical non-frail healthy individual as measured according to some embodiments of the disclosure.
Figure 7B:
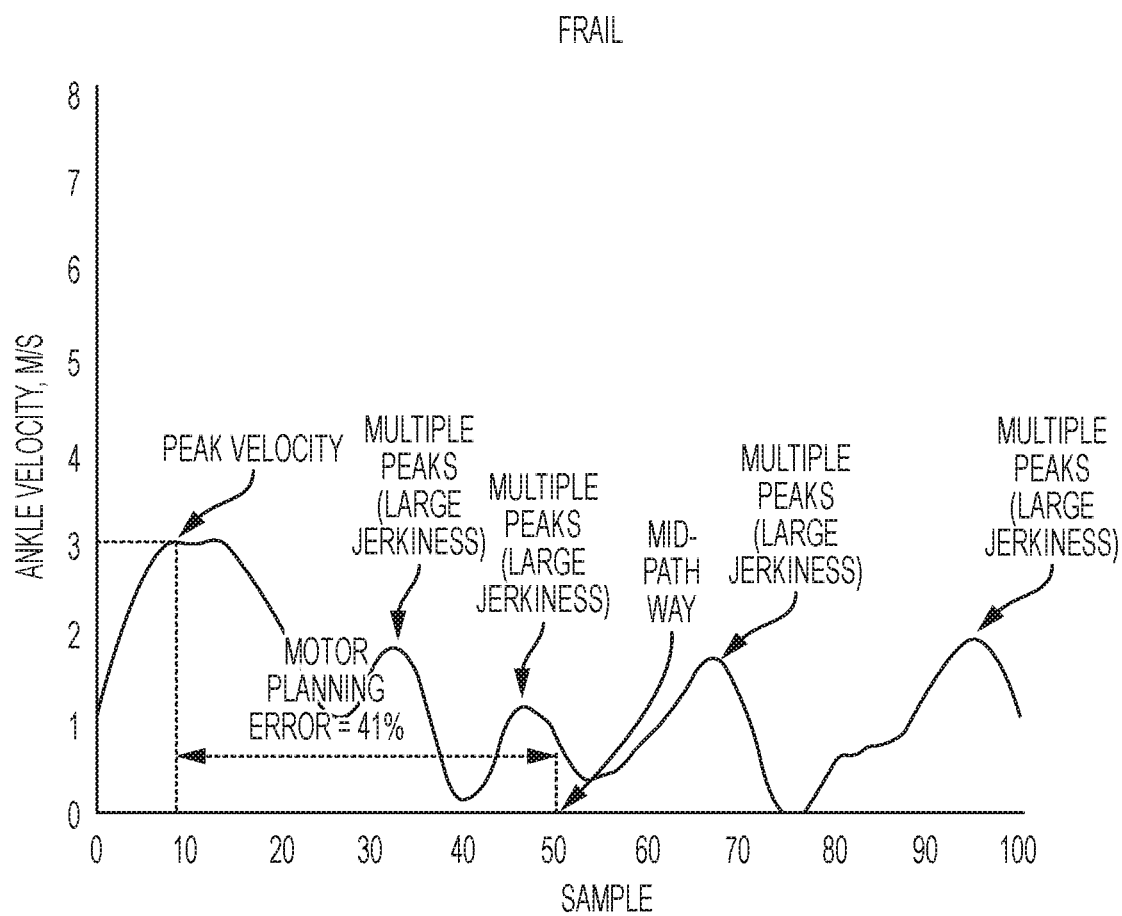
FIG. 7B is an illustration of a velocity pattern during point-to-point reaching task in a typical frail individual as measured according to some embodiments of the disclosure.

The iTMT platform may be configured to examine cognitive (e.g., trail-making performance) as well as motor ability (e.g., balance performance) of an individual and interaction between motor and cognitive performance (e.g., dual tasking) by examining the motion data from the wearable sensor 102. One embodiment of an iTMT platform was administered to examine the motor ability of individuals and discriminate between individuals with and without frailty. FIG. 6 is a graph illustrating the velocity pattern during a typical point-to-point reaching task. FIG. 7A is an illustration of a velocity pattern during point-to-point reaching task in a typical non-frail healthy individual as measured according to one embodiment of the disclosure. A large peak velocity and small motor planning error were observed. FIG. 7B is an illustration of a velocity pattern during point-to-point reaching task in a typical frail individual as measured according to one embodiment of the disclosure. A small peak velocity and large motor planning error, as well as multiple velocity peaks (large jerkiness of movement), were observed.

Figure 8B:
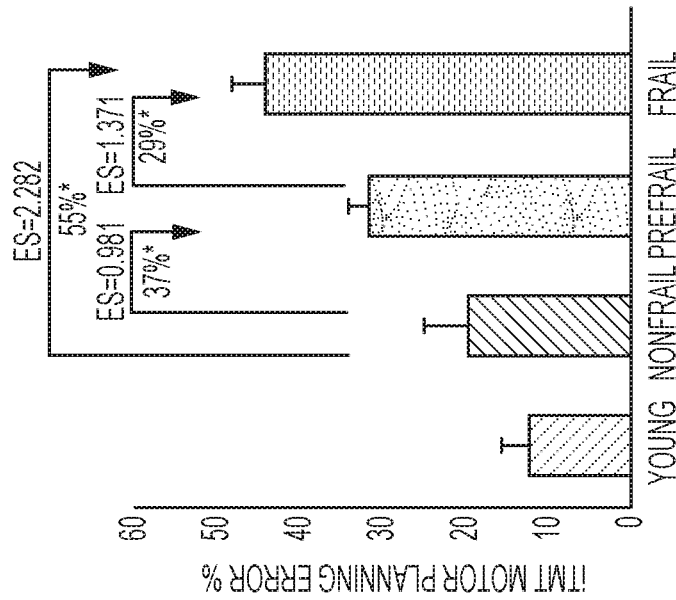
FIG. 8B is a graph illustrating using a motor planning error during instrumented trail-masking task (iTMT) neuropsychological test according to some embodiments of the disclosure to separate young, non-frail, pre-frail, and frail individuals.
Figure 8A:
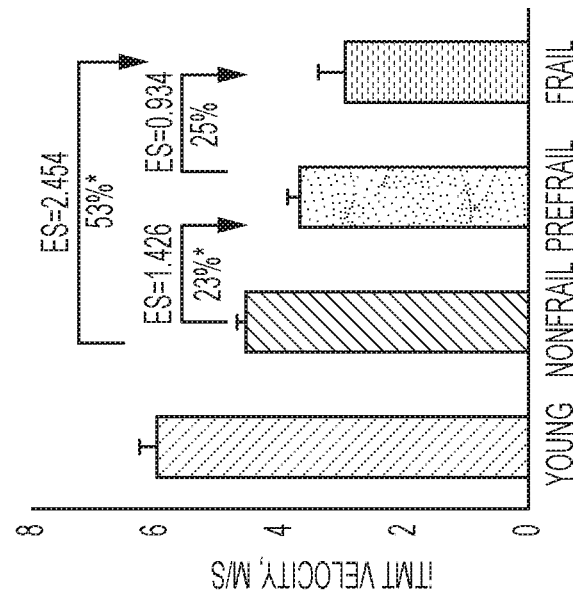
FIG. 8A is a graph illustrating using a peak velocity during instrumented trail-masking task (iTMT) neuropsychological test according to some embodiments of the disclosure to separate young, non-frail, pre-frail, and frail individuals.

One embodiment of an iTMT platform may be used to test subjects and identify subjects as non-frail, pre-frail, and frail individuals. The results of one such application are shown in and described with reference to FIG. 8A and FIG. 8B. Young, healthy individuals were included in the test population to show the differentiation with frail individuals. Some comparison data is shown in FIG. 8A, which is a graph illustrating using a peak velocity during instrumented trail-masking task (iTMT) neuropsychological test according to one embodiment of the disclosure to separate young, non-frail, pre-frail, and frail individuals. Significant differences between non-frail and pre-frail (mean difference=23%, effect size=1.426), as well as non-frail and frail (mean difference=53%, effect size=2.454) were observed. Some comparison data is shown in FIG. 8B, which is a graph illustrating using a motor planning error during instrumented trail-masking task (iTMT) neuropsychological test according to one embodiment of the disclosure to separate young, non-frail, pre-frail, and frail individuals. Significant differences between non-frail and pre-frail (mean difference=37%, effect size=0.981), non-frail and frail (mean difference=55%, effect size=2.282), as well as pre-frail and frail (mean difference=29%, effect size=1.371) were observed, as shown in FIG. 8B.

Figure 9A:
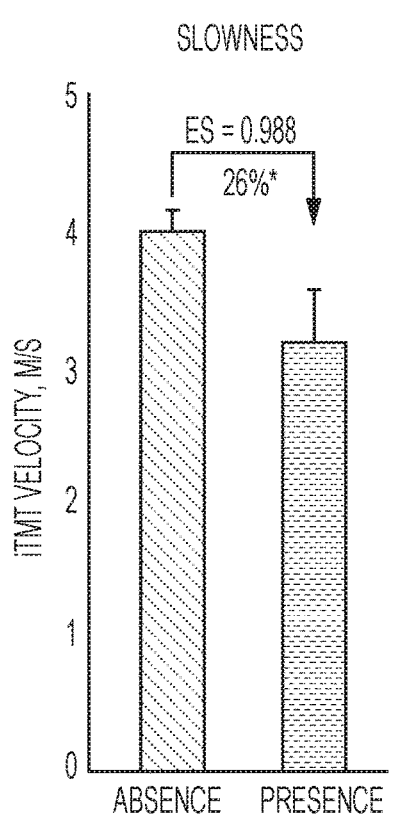
FIG. 9A is a graph illustrating using a peak velocity during instrumented trail-masking task (iTMT) neuropsychological test according to some embodiments of the disclosure to identify the presence and absence of slowness.
Figure 9B:
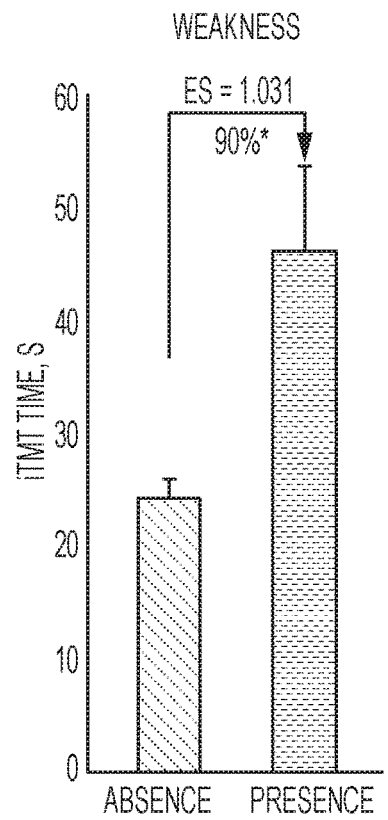
FIG. 9B is a graph illustrating using a completion time during instrumented trail-masking task (iTMT) neuropsychological test according to one embodiment of the disclosure to identify the presence and absence of weakness.
Figure 9C:
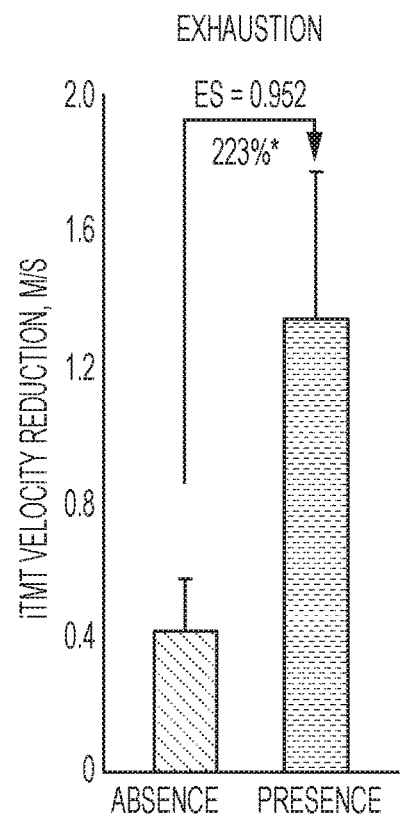
FIG. 9C is a graph illustrating using a velocity reduction during instrumented trail-masking task (iTMT) neuropsychological test according to one embodiment of the disclosure to identify the presence and absence of exhaustion.

One embodiment of an iTMT platform may be applied to test physical markers of motor impairment, such as slowness, weakness, and exhaustion. The results of one administration of such a configured iTMT platform is shown in and described with reference to FIG. 9A and FIG. 9B. FIG. 9A is a graph illustrating using a peak velocity during instrumented trail-masking task (iTMT) neuropsychological test according to one embodiment of the disclosure to identify the presence and absence of slowness. Significant difference (mean difference=26%, effect size=0.988) was observed. FIG. 9B is a graph illustrating using a completion time during instrumented trail-masking task (iTMT) neuropsychological test according to one embodiment of the disclosure to identify the presence and absence of weakness. Significant difference (mean difference=90%, effect size=1.031) was observed, as shown in FIG. 9B, indicating that the iTMT platform is capable of differentiating these characteristics between the subjects. FIG. 9C is a graph illustrating using a velocity reduction during instrumented trail-masking task (iTMT) neuropsychological test according to one embodiment of the disclosure to identify the presence and absence of exhaustion. Significant difference (mean difference=223%, effect size=0.952) was observed, as shown in FIG. 9C, indicating that the iTMT platform is capable of differentiating these characteristics between the subjects.

Some embodiments of the iTMT platform may implement a computerized routine, which makes the platform easy to use for non-experts. Because the platform incorporates a wearable sensor and a standard computing device, the platform may be deployed nearly anywhere, irrespective of setting. The iTMT platform provides objective metrics to identify cognitive-motor impairment, which can reduce the bias from the examiner with potential to track changes in cognitive-motor impairment over time. Furthermore, the iTMT results may not be affected by the individual's age and body-mass index (BMI), which makes it easier for routine applications and interpretation of results.

In some embodiments, the iTMT platform may be configured to implement dual-task tests, which may be used for evaluating the interaction between cognitive impairment and motor performance. Such interaction may be important to evaluate risk of falling and functional independency of the tested subject. One such dual-task test may include walking gait analysis. Dual task cost, the gait-speed difference between walking alone and walking while counting backward, can be a cognitive-motor indicator, which can predict an individual's decline in cognition and daily motor tasks. However, to identify the cognitive impairment in older adults, gait analysis may not be a feasible method. Many older population cannot walk independently, and need to use a cane, crutch, or walker while moving. This would greatly bias the result of using gait data identifying cognitive impairment. Pre-frail and frail are common phenomenon among older adults. Some subjects are too weak to walk at all or to walk enough distance (usually more than 20 meters) for collecting gait data. Further, gait assessment is often impractical for a small and busy clinic, which may not have adequate space or time to administer a walking test and in particular for a home setting, which may be unlikely to find an appropriate location without an obstacle for gait test. However, using embodiments of the iTMT platform described herein may provide a more practical tool for determining dual task cost and provide an estimate of gait parameters without the need of administrating a gait test.

The iTMT platform may also be configured to assess a subject during different postures (e.g., sitting, lying, or standing). By comparing the iTMT performance between two or more postures, the accuracy for identifying motor and cognitive impairment could be improved. Unlike dual-task walking, administration of this test is easy and safe. In addition, no dedicated space is required. Thus, dual-task tests with the iTMT platform are more suitable for routine assessment, irrespective of setting. In our results, with progression in cognitive impairment, a trend in increasing history of fall and frailty symptom was found. This demonstrates the potential ability of the iTMT platform to identify frailty and track motor performance decline.

In some embodiments, the iTMT platform may be configured in different manners to change the type of data collected. For example, comparison of motor performance during up-down reaching task and side reaching task during iTMT may be used to assess ankle stability and dynamic balance and reported to the individual. Furthermore, by changing the distance between a point-to-point reaching task during the iTMT test, joint flexibility and/or fear of falling may be assessed and reported to the individual. As another example, one or more additional cognitive and/or distractive tasks may be added to the iTMT and presented to the individual to increase the degree of cognitive complexity, such as by requesting counting backward during the iTMT test, and/or reaching to specific color code, shape, etc. targets instead or in addition to number/letter indexed targets.

The schematic flow chart diagram of FIG. 3 is generally set forth as a logical flow chart diagram. As such, the depicted order and labeled steps are indicative of aspects of the disclosed method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagram, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The operations described above as performed by a controller may be performed by any circuit configured to perform the described operations. Such a circuit may be an integrated circuit (IC) constructed on a semiconductor substrate and include logic circuitry, such as transistors configured as logic gates, and memory circuitry, such as transistors and capacitors configured as dynamic random access memory (DRAM), electronically programmable read-only memory (EPROM), or other memory devices. The logic circuitry may be configured through hard-wire connections or through programming by instructions contained in firmware. Further, the logic circuitry may be configured as a general purpose processor capable of executing instructions contained in software. If implemented in firmware and/or software, functions described above may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise random access memory (RAM), read-only memory (ROM), electrically-erasable programmable read-only memory (EEPROM), compact disc read-only memory (CD-ROM) or other optical disk storage, magnetic disk storage or other magnetic storage devices, or any other medium that can be used to store desired program code in the form of instructions or data structures and that can be accessed by a computer. Disk and disc includes compact discs (CD), laser discs, optical discs, digital versatile discs (DVD), floppy disks and Blu-ray discs. Generally, disks reproduce data magnetically, and discs reproduce data optically. Combinations of the above should also be included within the scope of computer-readable media.

In addition to storage on computer readable medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims.

Although the present disclosure and certain representative advantages have been described in detail, it should be understood that various changes, substitutions and alterations can be made herein without departing from the spirit and scope of the disclosure as defined by the appended claims. For example, although cognitive-motor impairment testing is described for the iTMT platform, the platform may also be used for cognitive-motor exercise training, assessing risk of falling, predicting outcomes post-intervention, screening outcomes, predicting adverse events such as delirium, studying the brain, and/or evaluating dual tasking on certain brain region activation. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method, comprising:
presenting, by a processor on a display, a series of requested motions to be performed by an individual;
receiving, by the processor, first motion data from a sensor worn by the individual, the first motion data recording movement of a body-joint of the individual performing a first instance of the series of requested motions while the individual is in a first posture, wherein the movement of the body-joint moves a cursor presented on the display while a sight-line between the sensor and the display is obstructed;
receiving, by the processor, second motion data from the sensor, the second motion data recording movement of the body-joint of the individual performing a second instance of the series of requested motions while the individual is in a second posture different than the first posture;
analyzing, by the processor, the first and second motion data to determine an impairment score for the individual indicative of an interaction between cognitive impairment and motor performance of the individual, wherein analyzing the first and second motion data comprises:
determining a first value of a parameter associated with a velocity of the cursor during the first instance of the series of requested motions, wherein determining the first value includes determining a first frequency component of a first signal corresponding to the velocity of the cursor during the first instance, determining a second frequency component of the first signal, and determining the first value as a ratio between the first and second frequency components of the first signal, wherein a frequency corresponding to the first frequency component is greater than a frequency corresponding to the second frequency component, and
determining a second value of the parameter associated with a velocity of the cursor during the second instance of the series of requested motions, wherein determining the second value includes determining a first frequency component of a second signal corresponding to the velocity of the cursor during the second instance, determining a second frequency component of the second signal, and determining the second value as a ratio between the first and second frequency components of the second signal;
determining, by the processor, the impairment score based on a comparison between the first and second values of the parameter, wherein the parameter is a jerkiness of the movement of the body-joint; and
reporting, by the processor, the impairment score for the individual.

2. The method of claim 1, wherein the step of presenting the series of requested motions comprises presenting a series of sequentially-ordered numbers in a fixed order on a display.

3. The method of claim 1, wherein the step of presenting the series of requested motions comprises presenting a series of sequentially-ordered numbers in a random order on a display.

4. The method of claim 1, wherein the step of presenting the series of requested motions comprises presenting a series of sequentially-ordered numbers and letters in a random order on a display.

5. The method of claim 1, wherein the step of presenting the series of requested motions comprises presenting a series of objects on a display.

6. The method of claim 1, wherein the step of analyzing the first and second motion data comprises determining a total time used by the individual to complete the series of requested motions in each of the first and second instances, and wherein the impairment score is determined based on a comparison between the total time used in the first instance and the second instance.

7. The method of claim 1, wherein the step of analyzing the received motion data comprises:
comparing a number of mistakes in performing the first instance of requested motions and the second instance of requested motions to determine a working memory performance; and
comparing a time elapsed between onset of movement and onset of display of virtual targets on the screen in performing the first instance of requested motions and the second instance of requested motions to estimate the ability of visual search, scanning, speed of processing, mental flexibility, and/or executive functions.

8. The method of claim 1, wherein the series of requested motions is point-to-point reaching to assess motor performance or frailty.

9. The method of claim 1, wherein the parameter associated with the velocity of the cursor is a dislocation of the maximum peak velocity of the cursor with respect to a middle pathway of a point-to-point reaching task to assess cognitive impairment, motor impairment, or fatigue.

10. The method of claim 1, wherein the jerkiness of the movement of the body-joint is associated with weakness and motor performance of the individual.

11. The method of claim 1, wherein the step of reporting the cognitive-motor impairment score comprises determining whether an individual exhibits signs of cognitive impairment, motor impairment, physical frailty, cognitive frailty, or a combination thereof.

12. The method of claim 1, wherein:
the first and second instances of the series of requested motions to be performed by the individual comprises requests for performing body movements, comprising a point-to-point reaching movement, that translates a motion of a body joint into an interactive interface, wherein the parameter is a jerkiness of the point-to-point reaching movement;
wherein determining the impairment score is further based on a comparison between first and second values of a second parameter and a comparison between first and second values of a third parameter, wherein the first values of each of the second and third parameters are associated with the first instance of the series of requested motions and the second values of each of the second and third parameters are associated with the second instance of the series of requested motions, wherein:
the second parameter includes a speed of a point-to-point reaching movement;
the third parameter includes a time to complete the series of requested motions; and
analyzing the received motion data to determine the impairment score for the individual comprises determining a separate cognitive performance score and motor performance score for the individual based on the comparison between the first and second values of the parameter, the comparison between the first and second values of the second parameter, and the comparison between the first and second values of the third parameter.

13. A computer program product comprising:
a non-transitory computer readable medium comprising code, which when executed by a processor, causes the processor to perform operations for performing steps comprising:
presenting a series of requested motions to be performed by an individual;
receiving first motion data from a sensor worn by the individual, the first motion data recording movement of a body-joint of the individual performing a first instance of the series of requested motions while the individual is in a first posture, wherein the movement of the body-joint moves a cursor presented on the display while a sight-line between the sensor and the display is obstructed;
receiving second motion data from the sensor, the second motion data recording movement of the body-joint of the individual performing a second instance of the series of requested motions while the individual is in a second posture different than the first posture;
analyzing the first and second motion data to determine an impairment score for the individual indicative of an interaction between cognitive impairment and motor performance of the individual, wherein analyzing the first and second motion data comprises:
determining a first value of a parameter associated with a velocity of the cursor during the first instance of the series of requested motions, wherein determining the first value includes determining a first frequency component of a first signal corresponding to the velocity of the cursor during the first instance, determining a second frequency component of the first signal, and determining the first value as a ratio between the first and second frequency components of the first signal, wherein a frequency corresponding to the first frequency component is greater than a frequency corresponding to the second frequency component, and
determining a second value of the parameter associated with a velocity of the cursor during the second instance of the series of requested motions, wherein determining the second value includes determining a first frequency component of a second signal corresponding to the velocity of the cursor during the second instance, determining a second frequency component of the second signal, and determining the second value as a ratio between the first and second frequency components of the second signal;
determining the impairment score based on a comparison between the first and second values of the parameter, wherein the parameter is a jerkiness of the movement of the body-joint; and
reporting the impairment score for the individual.

14. The computer program product of claim 13, wherein the step of presenting the series of requested motions comprises presenting a series of sequentially-ordered numbers in a fixed order on a display.

15. The computer program product of claim 13, wherein the step of presenting the series of requested motions comprises presenting a series of sequentially-ordered numbers in a random order on a display.

16. The computer program product of claim 13, wherein the step of presenting the series of requested motions comprises presenting a series of sequentially-ordered numbers and letters in a random order on a display.

17. The computer program product of claim 13, wherein the step of presenting the series of requested motions comprises presenting a series of objects on a display.

18. The computer program product of claim 13, wherein the step of analyzing the first and second motion data comprises determining a total time used by the individual to complete the series of requested motions in each of the first and second instances, and wherein the impairment score is determined based on a comparison between the total time used in the first instance and the second instance.

19. The computer program product of claim 13, wherein the step of analyzing the received motion data comprises:
comparing a number of mistakes in performing the first instance of requested motions and the second instance of requested motions to determine a working memory performance; and
comparing a time elapsed between onset of movement and onset of display of virtual targets on the screen in performing the first instance of requested motions and the second instance of requested motions to estimate the ability of visual search, scanning, speed of processing, mental flexibility, and/or executive functions.

20. The computer program product of claim 13, wherein the step of reporting the cognitive-motor impairment score comprises determining whether an individual exhibits signs of Mild Cognitive Impairment (MCI) or Alzheimer's Disease (AD).

21. The computer program product of claim 13, wherein the series of requested motions is point-to-point reaching to assess motor performance or frailty.

22. The computer program product of claim 13, wherein the parameter associated with the velocity of the cursor is a dislocation of the maximum peak velocity of the cursor with respect to a middle pathway of a point-to-point reaching task to assess cognitive impairment, motor impairment, or fatigue.

23. The computer program product of claim 13, wherein the jerkiness of the movement of the body-joint is associated with weakness and motor performance of the individual.

24. The computer program product of claim 13, wherein the step of reporting the impairment score comprises determining whether an individual exhibits signs of cognitive impairment, motor impairment, physical frailty, cognitive frailty, or a combination thereof.

25. A system, comprising:
a display;
a wearable sensor comprising at least one motion sensor, wherein the wearable sensor is configured to record motion data from the at least one motion sensor and to transmit the motion data; and
a computing device configured to receive the motion data transmitted by the wearable sensor and configured to perform steps comprising:
presenting, on the display, a series of requested motions to be performed by an individual;
receiving first motion data from the wearable sensor, the first motion data recording movement of a body-joint of the individual performing a first instance of the series of requested motions while the individual is in a first posture, wherein the movement of the body-joint moves a cursor presented on the display while a sight-line between the sensor and the display is obstructed;
receiving second motion data from the wearable sensor, the second motion data recording movement of the body-joint of the individual performing a second instance of the series of requested motions while the individual is in a second posture different than the first posture;
analyzing the first and second motion data to determine an impairment score for the individual indicative of an interaction between cognitive impairment and motor performance of the individual, wherein analyzing the first and second motion data comprises:
determining a first value of a parameter associated with a velocity of the cursor during the first instance of the series of requested motions, wherein determining the first value includes determining a first frequency component of a first signal corresponding to the velocity of the cursor during the first instance, determining a second frequency component of the first signal, and determining the first value as a ratio between the first and second frequency components of the first signal, wherein a frequency corresponding to the first frequency component is greater than a frequency corresponding to the second frequency component, and
determining a second value of the parameter associated with a velocity of the cursor during the second instance of the series of requested motions, wherein determining the second value includes determining a first frequency component of a second signal corresponding to the velocity of the cursor during the second instance, determining a second frequency component of the second signal, and determining the second value as a ratio between the first and second frequency components of the second signal;
determining the impairment score based on a comparison between the first and second values of the parameter, wherein the parameter is a jerkiness of the movement of the body-joint; and
reporting the impairment score for the individual.

26. The system of claim 25, wherein the step of presenting the series of requested motions comprises presenting a series of sequentially-ordered numbers in a fixed order on the display.

27. The system of claim 25, wherein the step of presenting the series of requested motions comprises presenting a series of sequentially-ordered numbers in a random order on a spatial display.

28. The system of claim 25, wherein the step of presenting the series of requested motions comprises presenting a series of sequentially-ordered numbers and letters in a random order on a spatial display.

29. The system of claim 25, wherein the step of presenting the series of requested motions comprises presenting a series of objects on the display.

30. The system of claim 25, wherein the step of reporting the cognitive-motor impairment score comprises determining whether an individual exhibits signs of Mild Cognitive Impairment (MCI) or Alzheimer's Disease (AD).

31. The system of claim 25, wherein the series of requested motions is point-to-point reaching to assess motor performance or frailty.

32. The system of claim 25, wherein the parameter associated with the velocity of the cursor is a dislocation of the maximum peak velocity of the cursor with respect to a middle pathway of a point-to-point reaching task to assess cognitive impairment, motor impairment, or fatigue.

33. The system of claim 25, wherein the jerkiness of the movement of the body-joint is associated with weakness and motor performance of the individual.

34. The system of claim 25, wherein the step of reporting the impairment score comprises determining whether an individual exhibits signs of cognitive impairment or motor impairment or both.

35. The system of claim 25, wherein the processing device is integrated with the wearable sensor.

* * * * *

UNITED STATES PATENT AND TRADEMARK OFFICE
CERTIFICATE OF CORRECTION

PATENT NO. : 12,011,282 B2
APPLICATION NO. : 16/334571
DATED : June 18, 2024
INVENTOR(S) : Bijan Najafi et al.

Page 1 of 1

It is certified that error appears in the above-identified patent and that said Letters Patent is hereby corrected as shown below:

On the Title Page

Item (71) Applicants: Arizona Broad of Regents on behalf of Arizona State University should read Arizona Board of Regents on Behalf of the University of Arizona Signed and Sealed this
Eighteenth Day of March, 2025

Coke Morgan Stewart
*Acting Director of the United States Patent and Trademark Office*